United States Patent
Craig et al.

(10) Patent No.: US 6,716,618 B1
(45) Date of Patent: Apr. 6, 2004

(54) VERMIPROCESS FOR ASBESTOS REMEDIATION

(75) Inventors: Jonathan Craig, Yakima, WA (US); G. Daniel Thomas, Yakima, WA (US)

(73) Assignee: Good Earth Solutions, LLC, Yakima, WA (US)

( * ) Notice: Subject to any disclaimer, the term of this patent is extended or adjusted under 35 U.S.C. 154(b) by 0 days.

(21) Appl. No.: 10/369,946

(22) Filed: Feb. 18, 2003

(51) Int. Cl.[7] .................................................. B09B 3/00

(52) U.S. Cl. ........................ 435/262.5; 71/9; 71/25

(58) Field of Search .................. 435/262, 262.5; 71/9, 25

(56) References Cited

U.S. PATENT DOCUMENTS

| | | | | | |
|---|---|---|---|---|---|
| 4,108,625 | A | * | 8/1978 | Okada | 71/9 |
| 4,285,719 | A | * | 8/1981 | Criss | 71/13 |
| 4,971,616 | A | * | 11/1990 | Glogowski | 71/9 |
| 5,082,486 | A | * | 1/1992 | Glogowski | 71/9 |

OTHER PUBLICATIONS

Schreier, H. et al., "Earthworm Response to Asbestos–Rich Serpentinite Sediments", Jul. 15, 1985, Soil. Biol. Biochem. vol. 18, No. 1, pp. 85–89.*

* cited by examiner

Primary Examiner—David A. Redding
(74) Attorney, Agent, or Firm—Stratton Ballew PLLC

(57) ABSTRACT

A system and process for remediating an "asbestos containing material" (ACM), or a "regulated" asbestos containing material (RACM), with a vermicultural process, or "vermiprocess." Worms are employed to convert the ACM into a material with an acceptable, deminimus level of asbestos fibers, or further to a non-detectable level of asbestos. The process includes placing an asbestos containing material into a worm bin and mixing the asbestos containing material with an effective quantity of a worm adjuvant, optionally employing organic material and mixing in a homogenizer. The worm bin may be a single bin or alternatively an array of staged worm bins. The worms are introduced into the ACM to form an asbestos containing vermicompost. The preferred worm species employed the species *Esenia hortensis*, or "hortensis," and *Esenia fetida*, commonly referred to as "red wigglers," or "red worms." The processing of the asbestos containing material with the worms includes the ingestion of the asbestos containing materials by the worms to forming a vermiprocessed product. The product may be liquified and micronized for disposal for further processing.

16 Claims, 2 Drawing Sheets

Note: dashed lines represent process alternatives

Note: dashed lines represent process alternatives

VERMIPROCESS FOR ASBESTOS REMEDIATION

TECHNICAL FIELD

The invention relates to a process for a system employing worms to process an asbestos containing material (ACM). The vermiprosessing system of the present invention includes a vermicomposting technique for reducing the asbestos fiber content of the ACM, with the ability to convert the material into a non-regulated ACM, or further process the ACM into an asbestos free material.

BACKGROUND OF THE INVENTION

"Asbestos" is a generic term, commonly employed in a broad reference to the fibrous or "asbestiform" varieties of naturally occurring minerals, which fall into two groups: Serpentinite, commonly referred to as "chrysotile," and amphibloe, which includes rebecktite, also referred to as "crocidolite," cummongtonite-grunerite, also referred to as "amosite," and anthophyllite, actinolite and tremolite asbestos. Typically, asbestos materials possess the desirable qualities of high tensile strength, flexibility, and resistance to chemical and thermal degradation. Asbestos is also a superior insulator, due to its high electrical resistance and low heat transfer. These properties have made asbestos a popular component for a variety of commercial and industrial products, from automotive brake pads and protective suits for firefighters, to home siding and boiler insulation.

On a microscopic level, the asbestos mineral is fibrous in structure. Asbestos fibers naturally form bundles or "fibrils," which are long and thin, and separate easily. Because of their fibrous structure, asbestos fibers are relatively easy to observe and count. Employing "polarized light microscopy," or PLM techniques, asbestos fibers are accurately identified. Asbestos fibers exhibit a dramatic response to polarized light, especially when enhanced with specific, high refractive index oils. Standards for the identification and quantitative analysis of asbestos in materials are well documented in applicable government regulations and microscopy texts. Specifically, methods EPA/600/R-93/116 and EPA/600/M8-82-020, are current standards for the determination of asbestos in bulk insulation materials.

This high level of scrutiny of "asbestos containing material" (ACM), stems from the fact that most health and public safety agencies deem airborne asbestos fibers a substantial health risk and hazard. According to the United States Environmental Protection Agency (EPA), asbestos is a toxic substance and a known carcinogen. Although it is commonly accepted that most people do not become ill from normal, background levels of asbestos, asbestos exposure is considered a health concern when high concentrations of asbestos fibers are inhaled over a long period of time. The EPA has established a series of stringent regulations, as mandated by the Clean Air Act of 1984, which strictly require a proper handling of ACM. The primary regulation in this regard is found in 40 CFR, Chapter I of the "National Emission Standards for Hazardous Air Pollutants" (NESHAP), specifically the part beginning at §61.140, titled "Subpart M—National Emission Standards for Asbestos," and collectively referred to herein as "Asbestos NESHAP."

To minimize the potential for public exposure to elevated levels of asbestos fibers, when asbestos materials are encountered in demolition or construction, the current regulations, which include the Asbestos NESHAP, require extensive safeguards in the removal and handling of asbestos and materials that contain asbestos. ACM is typically present in some component of any modem building or ship, manufactured prior to the public scrutiny of asbestos as a health risk. These suspect components typically include the wrapping of any vessel, tank, boiler, heat pipe or duct. The regulations focus care and concern on the ACM that most likely presents a public health threat. Specifically, when ACM is encountered in demolition, renovation or construction activities, the EPA first requires identification of asbestos containing materials, all of which must be handled in accordance to the Asbestos NESHAP as a "regulated asbestos containing material" (RACM). This material is often removed, rather than "encapsulated" and maintained in place, as a preventative measure to minimize the potential for public exposure to elevated levels of asbestos fibers.

Presently, most asbestos removal is performed by certified workers employing manual methods and procedures, as required under the Asbestos NESHAP. Such manual methods include gloves and simple hand tools. Prohibited, mechanical removal methods tend to abrade, grind or in some way pulverize the ACM. Typically, the ACM is carefully moistened, manually removed, and placed into bags. The bags are then transported to a landfill certified for the receipt of such materials. However, this disposal process is time consuming and expensive. The bags must be handled several times on the way to a safe disposal. The risk of breakage or loss in transport is significant Additionally, a land fill's RACM disposal fees are prohibitively expensive. This high expense arises in part from the liability and safety issues associated with such disposal, and the strict regulatory oversight for RACM disposal. Because of the expense of proper RACM disposal, the unscrupulous may be tempted to circumvent the rules and improperly remove and illegally dispose of RACM, generating much more of an environmental problem than if the asbestos was left in place and undisturbed.

Besides landfills, other method for the disposal of asbestos have been proposed and implemented with varied success. An example is U.S. Pat. No. 4,678,493 to Roberts et al., which discloses an asbestos waste vitrification process. High temperature vitrification or "glasifying," at temperatures above 1000° C., is employed to literally melt asbestos into a glass at high temperatures, rendering it safe for conventional disposal in a landfill. This process apparently works very well on pure asbestos and mineral asbestos mixtures. However, only a small percentage of a typical ACM is asbestos. Most of the ACM is non-mineral, non-asbestos material. Hazardous combustion products from plastics, cellulose materials and organic toxics represent a threat to public health and so are a great concern to regulators. The efficient and effective removal of airborne, unprocessed asbestos from the fly ash, are all significant issues that prevent the widespread use of this process.

Chemical treatment processes that degrade asbestos have also been developed to remediate ACM. U.S. Pat. Nos. 6,005,158 and 6,160,195 to Sugama et al., disclose the use the use of a "super acid" mixture, including concentrated fluoric and phosphoric acids. The super acid is apparently able to digest asbestos containing materials, converting them into environmentaily benign components, predominantly comprising quartz.

In any event and regardless of the conventional or unconventional method employed, the safe and effective removal and disposal of RACM is time consuming and expensive. The safety and expense of the incineration and acid digestion are apparent, as discussed above. These unconventional processes, as well as the conventional removal and landfill disposal methods are fraught with procedural difficulties. Complexity and expense opens many opportunities for mismanagement, with a high likely-hood of failures in oversight and error, resulting in accidental release of asbestos fibers to the air. The fact of the matter is that the landfilling of asbestos may only be a short term solution with a chain of liability traceable to every handler and owner of the ACM. A safer, permanent, more effective and more economical process for the remediation and disposal of ACM is needed.

Recently, the common earthworm has become increasingly popular for use as a composting agent in the processing of organic waste materials. Earthworms readily digest food waste or similar debris, often mixed with paper and other organic materials to form an "organic feed stock." The organic feed stock is ingested by the worms over time to produce a compost product that is especially suitable for garden soil or farm tillage. A conventional worm composting, or "vermicomposting" operation centers around a "worm bin," which is a container for housing the combined worms and organic feed stock.

U.S. Pat. No. 4,108,625, to Okada discloses a worm bin apparatus that efficiently composts vegetable matter with the worms to produce a natural, organic fertilizer. U.S. Pat. No. 4,285,719 to Criss also discloses an organic material recycling device that employs a worm organism, specifically "Esenia fetida," to compost human solid waste.

The use of earthworms for composting on a large scale has also been considered. U.S. Pat. Nos. 4,971,6161 and 5,082,486 to Glowgowski describes the processing of municipal garbage with a regenerating earthworm bed.

However, the actual use of earth worms for processing feedstocks other than the organic materials conventionally utilized in vermicomposting, has met considerable difficultly. This is especially true in any attempts to introduce toxic substances to the worms, in hopes that the worms could somehow ingest these toxic materials and render them safe, or environmentally benign. However, the worms, being living organisms, are sensitive to toxins. The processing of toxic materials by vermicomposting has universally resulted in severe impacts upon the health of the worms, and more typically to the death of the worms so employed.

Asbestos, as discussed above, is a toxic material. Not only is asbestos apparently toxic to humans, but it has been asserted as being fatal to the common earthworm varieties employed in conventional vermicomposting. A study titled "Earthworm Response to Asbestos-Rich Serpentinitic Sediments," performed at the University of British Columbia, in Vancouver B.C., Canada, by the Department of Soil Sciences, as published in the *Journal of Soil Biology and Biochemistry*, Vol. 18, No. 1, pp 85–90 (1986), attempted to process asbestos containing soils with common earthworms of the variety *Lumbricus ruhellus*. The mortality rates of the worms were dramatic, and analysis of the short survived worms showed high levels of asbestos within. Just as a person skilled in the art of vermicomposting would likely expect, based upon the well established toxic nature of asbestos fibers, the worms were unable to effectively ingest and process asbestos.

Therefore, with the failings of these above experimenters and the apparent need for a truly safe and efficient method for the remediation of ACM, an apparatus or technique is still needed that provides an environmentally safe and efficient process of the remediation of ACM. The inventors of the present invention have addressed many of the issues as presented above in the development of a new method for asbestos remediation. The present invention will be better understood by reference to the following detailed description taken in conjunction with the accompanying drawings.

DETAILED DESCRIPTION OF SPECIFIC EMBODIMENTS

The present invention provides a system for remediating "asbestos containing material" (ACM), with a vermicultural process, or "vermiprocess." For vermiprocessing, worms are employed to convert the ACM into a material with an acceptable, deminimus level of asbestos fibers, or further to a non-detectable level of asbestos.

Figure 1:
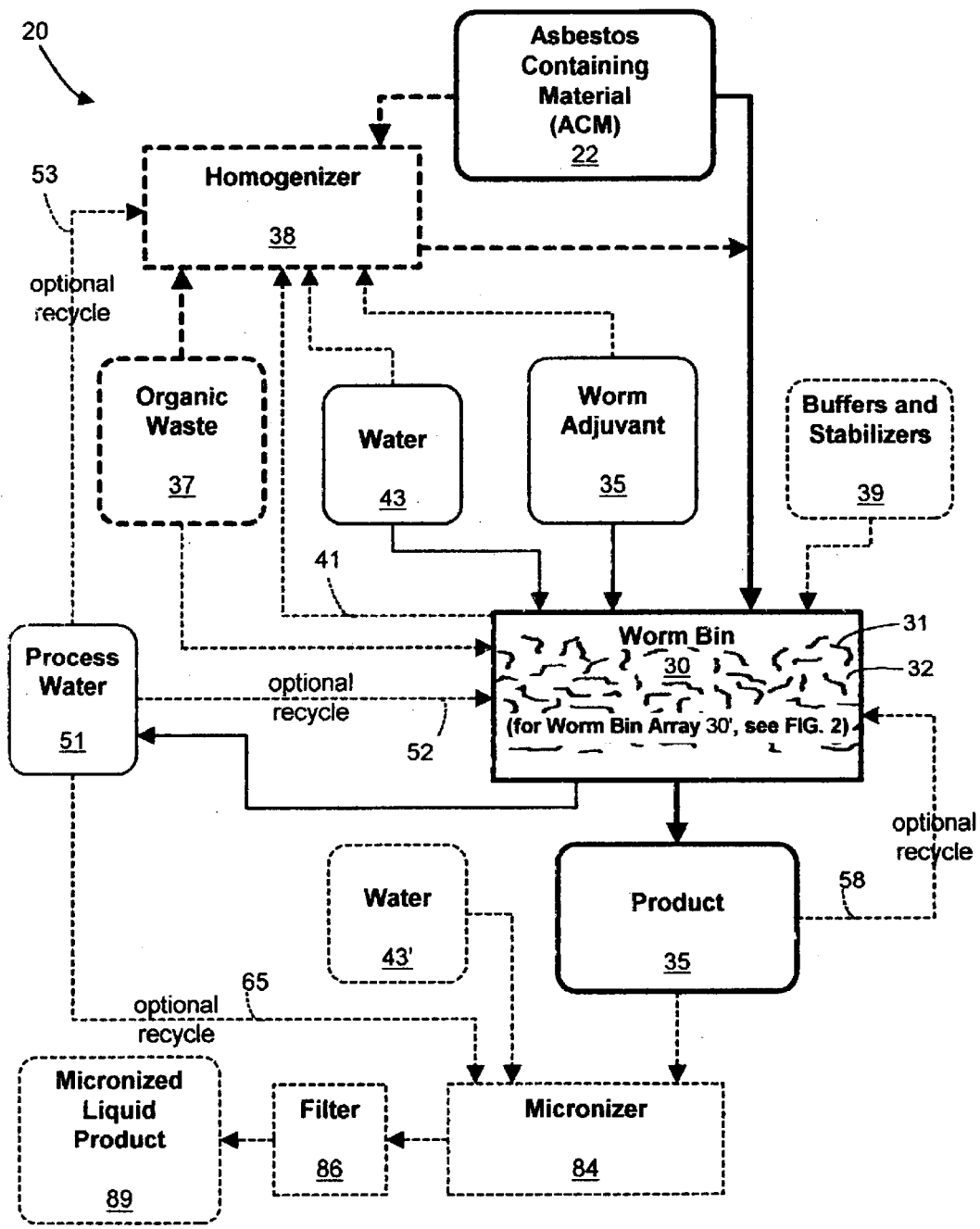
FIG. 1 is schematic diagram of a vermiprocess for asbestos remediation, according to an embodiment of the invention.
Figure 2:
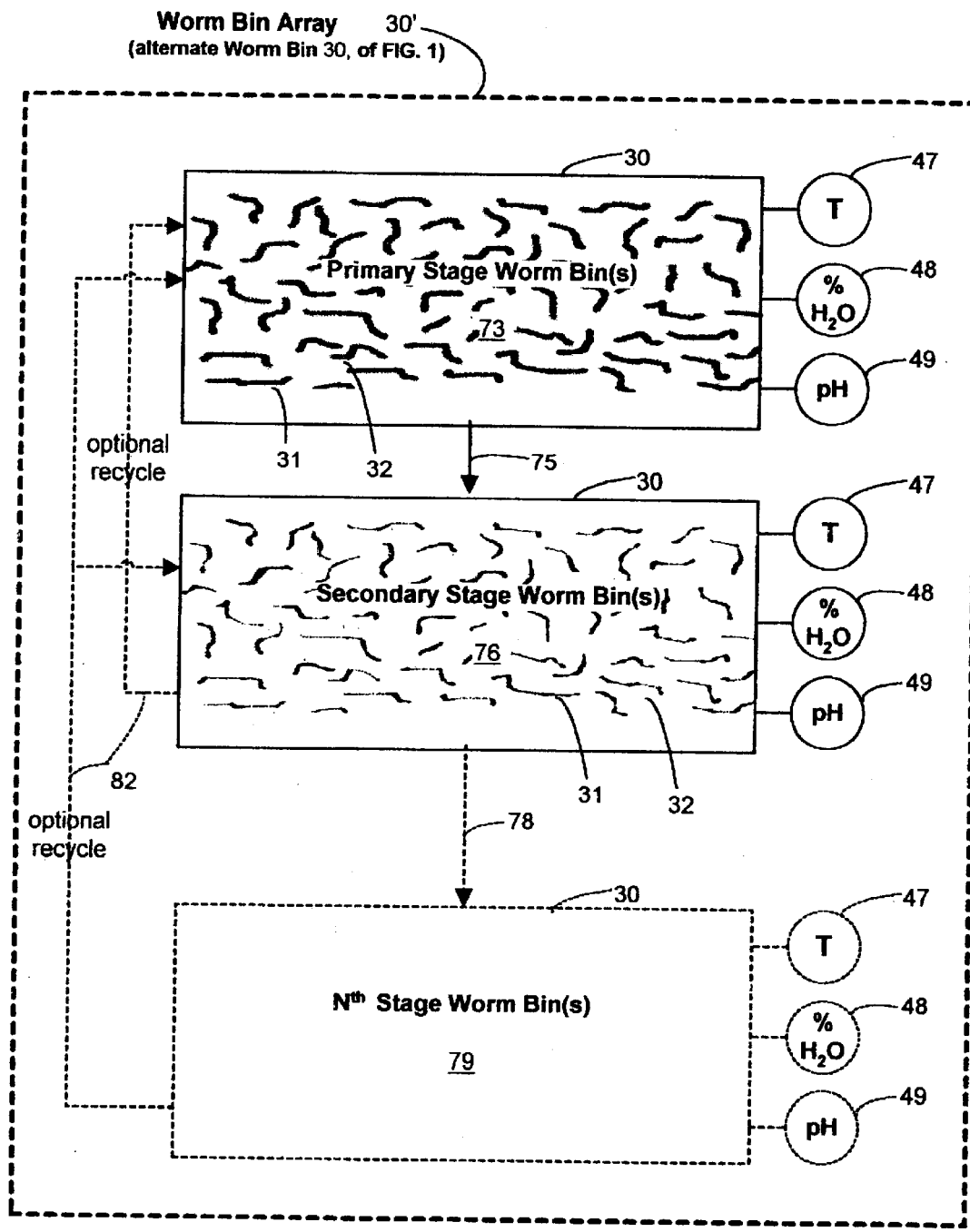
FIG. 2 is a schematic diagram of a portion of a vermiprocess for asbestos remediation, according to an embodiment of the invention.

Specific embodiments of an asbestos vermiprocessing system 20, according to the present invention, are shown in FIGS. 1 and 2. As shown in FIG. 1, the ACM 22 is introduced into worm bin 30, for processing by a plurality of worms 31. Within the worm bin, the ACM becomes an "asbestos vermicompost" 32, as additional materials are added to ACM. These additional material facilitate the ingestion of the ACM by the worms. The materials added to the worm bin to aid in processing the ACM preferably include a "worm adjuvant" 35.

The worm adjuvant 35 employed in the present invention is substantially a common mixture, often referred to in the art of vermiculture as a "compost tea." The standard worm adjuvant includes dietary supplements and ingestion aids, to best facilitate the action of the worms in a given compost material. Preferably, the worm adjuvant also includes microbes tailored for the digestive process of the worms. These microbes in the worm adjuvant can include an appropriate mixture of bacteria and fungal cultures, as desirable for the archiving and maintaining the worm at a state of optimum health. Additionally, the compost tea is "steeped," at a temperature of approximately 70° F. to 90° F., for the purpose of diffusing the nutrients and microbes into a solution that is aerated to facilitate beneficial, aerobic reactions. A preferred compost tea or worm adjuvant includes a suspension of aerobic bacterial and fungal cultures, with a variety of nutrients and other digestive aids. One preferred formulation is brewed with Compost Tea Catalyst™, as manufactured by Growing Solutions®, Inc., of Eugene Oreg. USA. Compost Tea Catalyst™ includes seaweed extract, humic acids, rock powder, and other botanical ingredients. The compost tea is preferably brewed in a conventional brewing device manufactured for such a purpose. A preferred device is an Earth Tea Brewer™, as manufactured by EPM, Inc., of Cottage Grove Oreg., USA.

As preferred alternative additions to the worm adjuvant 35, specifically for the purpose of supplementing the typically low nutritional value of the ACM, the inventors of the present process also include common molasses in the worm adjuvant mixture. Alternatively, any sugar, starch or carbohydrate can be included as a supplement to the worm adjuvant. Cane sugar, beet sugar, or potato, flour product and dairy product processing wastes, are all considered as potential alternatives to the molasses. Also, as an additional alternative addition to the worm adjuvant, the present inventors alternatively substitute finely ground glass for rock mineral ingredients, specifically for the purpose of aiding in the abrasive action of the ingestive processes of the worms 31.

In a preferred alternative to introducing the worm adjuvant 35 directly into the worm bin 30, the worm adjuvant can be placed into a separate container and pre-mixed with the ACM 22, prior to introduction into the worm bin. This mixing container can be referred to as a homogenizer 38, as shown schematically in FIG. 1. The homogenizer is preferably a mixing container or tub that includes a mixing device for thoroughly blending the contents of the homogenizer. Most preferably, this mixing is accomplished in compliance to the manual method requirements of the Asbestos NESHAP, without sawing or cutting, but by gently shearing the material within, as preferably performed by a simple auger mixing device. Also most preferably, the homogenizer is a closed vessel and can include a high efficiency particulate (HEPA) air filter for any effluent air or gases. A preferred, small scale homogenizer that is suited for use with the present invention is the Earth Tub™, as manufactured by Green Mountain Technologies, of Whitingham Vt., and Seattle Wash., USA.

A preferred alternative in the asbestos vermiprocessing system 20, includes the addition of an organic waste 37 to the worm bin 30. The addition of the organic waste serves the purpose of supplying the plurality of worms 31 in the worm bin with additional nutrients and food material, aiding in the ingestion of the ACM 22. Additionally, the organic waste is disposed of efficiently by the worms, as is accomplished in conventional vermicomposting systems. The organic waste can be any such material, again as known to those skill in vermicomposting and can include as organic refuse, compost, paper pulp, manure and agricultural products.

In a preferred alternative, the homogenizer 38 can be employed to pre-mix the organic waste with the ACM 22 and worm adjuvant 35. A water 43 can also be added to the worm bin 30, and optionally to the homogenizer, as shown in FIG. 1. Preferably, per standard methods of vermiculture, the vermicompost within the bin is maintained near an optimal moisture content, between approximately 55% and 65% water, by weight. The water is preferably introduced into the worm bin in a fine spray, to maintain the integrity of any friable ACM present in the worm bin, and keeping the ACM "adequately wet," as required under the Asbestos NESHAP.

For the asbestos vermiprocessing system 20, of the present invention, the plurality of worms 31 consume and break down the ACM 22 through the process of worm composting to form a product 55. With this asbestos vermiprocessing system 20, the microscopic "counts" of asbestos fibers in the product can fall well below statutory levels of concern. By further processing in the worm bin 30, in accordance to the methods of the present invention, the asbestos fiber content of the product can be further reduced to no detectable presence of asbestos fibers within the product material. According to the experiments so far performed, as typified by the examples discussed later herein, the processing activity of the plurality of worms appears to convert the ACM into an asbestos free material.

In a preferred embodiment of the present invention, as detailed in FIG. 1, the ACM 22 is placed directly into a worm bin 33. The worm bin can simply be referred to as a "bin," in that it can be simply embodied by a tub or container. The primary purpose of the bin is to confine an active worm population for performing the process of the present invention. The worm bin is preferably a conventional device of the type that is specifically manufactured for use in the processing of materials, with the aid of worms. To increase the efficiency of operation, these conventional worm bins can include many features specific to their specialized use. A preferred worm bin, especially suited to larger processing operations, the modular, industrial sized vermicomposting system, as manufactured by EPM, Inc., of Cottage Grove Oreg., USA., functions well for the purposes of the present invention.

Alternatively, for smaller scale operations, the worm bin 30 may be scaled down, and simpler in design. The operation and design of worm bins is well known to those skilled in vermicomposting. An ordinary, opaque plastic, wood or metal tub can be employed as the worm bin for the purposes of the present invention.

In a preferred embodiment of the present invention, the worm bin 30 includes monitoring devices to insure that the conditions within the worm bin are optimal for the processing by the worms of the ACM 22 containing vermicompost 32. Preferred monitoring devices are shown in FIG. 2, for use in each worm bin of the present process. The monitoring devices can include a thermometer 47, a water moisture meter 48 and a pH meter 49. These devices are standard, "off the shelf" instruments that are easily installed and preferably telemetered to a central monitoring station for the efficient operation of the asbestos vermiprocessing system 20. The optimal ranges of parameters, such as temperature, moisture and pH are well known indicators of worm health and can be adjusted by established methods to optimize the activity and health of the worms. The operation and use of devices like these described above, are well known to those skilled in vermicomposting and those in the field of worm health Adjustments to the operational conditions within the worm bin 30 are easily achieved Buffers and stabilizers 39 are an optional additive to the worm bin, preferably added in response to the needs of the worms 31, and therefore optimize the processing of the ACM 22 within the vermicompost 32. Such buffers and stabilizers are well known to those skilled in vermiculture. For instance, the pH balance within the worm bin can be adjusted to an optimal neutral value by the addition of mildly acidic or mildly basic compounds. Temperature within the worm bins can be increased with heaters. Water 43 can also be added, as needed.

Additionally, the worm bin 30 can includes a provision for drainage of excess liquid This excess liquid is a process water 51, that can be filtered to remove all possible asbestos and then can be recycled as a process water in an optional recycle 52 back into the worm bin 30. Alternatively, the water can be optionally recycled 53 into the homogenizer 38.

Preferably, the entire asbestos vermiprocessing system 20 of the present invention can be an enclosed system, sealed from the outside air in a negative air enclosure, per the requirements of the Asbestos NESHAP. Most preferably, the work space of the worm bin and all processing of ACM by the method of the present invention is performed within a "negative air enclosure," with respirator protection and full covering worn by all operational personnel within the enclosure.

As an alternative equivalent to enclosing the entire asbestos vermiprocessing system 20, the individual components of the system can be maintained under negative air pressure, each component exhaust HEPA filtered, again in compliance with pertinent regulations. For this alternative, the worm bin 30 can be a sealed unit, with the option of forced oxygen, or preferably air, supplied into the bottom of the bin. The static air pressure within the worm bin can be maintained at a negative pressure, relative to the ambient static air pressure, external to the worm bin. The negative air exhaust stream from the worm bin can then be filtered, preferably with HEPA filtration, assuring the removal of substantially all asbestos fibers that may be present in the exhaust stream.

Also alternatively, the ACM 22 processed by the asbestos vermiprocessing system 20, can be a regulated asbestos containing material (RACM) brought in from a remote site or processed on-site by the present invention. Under the Asbestos NESHAP, processing RACM at a remote site requires certification of the processing system employed, which must also comply with local regulations. The use of RACM in the present invention is preferred, in that such material is specifically defined by the Asbestos NESHAP, as "regulated" by containing more than 1% asbestos fibers, as determined in accordance to the laboratory standard PLM techniques, referenced, therein. Specifically, this term "RACM" is defined as including certain "Category I" and "Category II" ACM, as defined in §61.141 of the Asbestos NESHAP. Most preferably, the asbestos processing system of the present invention is built on site, to process materials generated directly from that specific remediation site, with a minimum of handling and transportation.

An important consideration for the present invention is selecting the optimum species of earthworm. The species *Esenia hortensis*, referred to herein as simply *"hortensis."* Hortensis is a preferred choice, in that this particular species is large, robust and ideal for the ingestive processing of relatively large bits of material, especially ACM. Another preferred species of earthworm for use with the process of the present invention is *Esenia fetida*, referred to herein as *"fetida,"* but more commonly referred to as "red wigglers," or as "red worms." These worms, as well as some of the other potential varieties likely suited for the purposes of the present invention can be purchased in bulk from VermiCo, of Grants Pass Oreg., USA, or Wormfarm com, of Yakima Wash., USA.

Worms 31 bred in a set, cultured environment are preferred for the present invention in that these worms can be initially propagated on a diet with components similar to the organic material present in the ACM 22 targeted for remediation with the asbestos vermiprocessing system 20. The present inventors found through experimentation that worms specifically bred and raised on a diet of cardboard pulp, were predisposed toward the ingestion of "air cell" pipe covering, which is a common, paper based ACM.

The species of worms 31 *"fetida"* are smaller than the *"hortensis,"* but are very robust and serve to actively ingest smaller bits of the ACM 22. The worm's activity also includes ingesting the castings of the *hortensis* and other *fetida*, as the worms collectively and aggressively breaking down and converting the ACM to a product 55. This product can be a non-ACM or asbestos free material, if the process of the present invention is allowed to proceed to a full breakdown and conversion of all ACM introduced.

As well understood by those skill in vermicomposting, others of the many different species of worms 31 could certainly have the potential to be employed in addition to, or in lieu of the species herein discussed as most preferred. Generally, all species of earthworms have some ability to adapt, especially of successive generations to whatever food supply is offered. However, the species and combinations of species of worm as discussed herein for use with the asbestos vermiprocessing system 20, appear to have the innate ability to ingest the potentially toxic ACM 22, and further to thrive with even significant quantities of ACM present in the worm bin 30.

According to a preferred method of the present invention, the selected species of worms 31 can be introduced to the worm bin 30 by spreading them over the surface of the vermicompost 32 in the worm bin. The worms are preferably covered with damp burlap, shredded paper, or similar material to keep the upper surface of the infeed material in the bin moist and warm.

In a preferred embodiment of the present invention, the worms 31 of the *fetida* species are utilized in combination with the *hortensis* species, in a common worm bin 30, with each processing materials best suited to the particular species. However, as a more preferred alternative to the common worm bin, especially for larger processing projects, the worm varieties can be placed in species specific bins of a bin array 30', as shown in FIG. 2. The bins are preferably placed in series to best exploit the potentially unique ingestive abilities and characteristics of each species of worm employed. This "staged" bin array optimizes each earthworm species individually, for an improved overall performance in processing the ACM 22.

As shown in FIG. 2, the worm bin array 30' can include a primary stage worm bin 73. The primary stage worm bin first receives the ACM 22, the water 43, the worm adjuvant 42, and the buffers and stabilizers 39, as discussed above in reference to the worm bin 30 of FIG. 1. As an alternative to a single, primary stage worm bin, the primary stage worm bin may be a multiple of bins or containers, as desired to process a given quantity and type of ACM.

The vermicompost 32 generated by the primary stage worm bin(s) 73 preferably serve as a secondary stage infeed 75 for a secondary stage worm bin 76, as also shown in FIG. 2. Besides the secondary stage infeed, the secondary stage worm bin can also receive additional ACM 22, water 43, worm adjuvant 42, and buffers and stabilizers 37, as discussed above in reference to the worm bin 30 of FIG. 1. Most preferably, the secondary stage worm bin only receives water 43, worm adjuvant 42, and buffers and stabilizers 37, in addition to the secondary stage infeed, because the asbestos un-processed by the primary stage worm bin is included in the secondary stage infeed. As with the primary stage worm bin, an alternative to a single secondary stage worm bin may be a multiple of bins or containers, as desired to process a given quantity and type of ACM.

Preferably, the optimum number of stages in the worm bin array 30' is two, with the single, primary stage worm bin 73 and single, secondary stage worm bin 76 However, additional stages are considered, up to an "nth" stage worm bin 79, as shown in FIG. 2. The secondary stage worm bin(s) serve as an nth stage infeed 78 for the nth stage worm bin. Besides the nth stage infeed, the nth stage worm bin can also receive additional ACM 22, water 43, worm adjuvant 42, and buffers and stabilizers 37, as discussed above in reference to the worm bin 30 of FIG. 1. Most preferably, the nth stage worm bin only receives water 43, worm adjuvant 42, and buffers and stabilizers 37, in addition to the nth stage infeed, because the asbestos unprocessed by the secondary stage worm bin is included in the nth stage infeed. As with the primary and secondary stage worm bin, an alternative to a single nth stage worm bin may be a multiple of bins or containers, as desired to process a given quantity and type of ACM.

As an alternative in the operation of the worm bin array 30', the vermicompost 31 of any worm bin 30 in the array may be recycled to a prior stage worm bin. For example, as shown in FIG. 2, vermicompost from the secondary stage worm bin 74 can be returned to the primary stage worm bin in an optional recycle 82.

Though the following examples were performed on a small scale, the techniques preferred or larger processing through-puts are substantially the same and so the scale of the process of the present invention is not considered critical, but the process as described in the claims that follow the examples.

EXAMPLE 1

5.75 pounds of an ACM 22 was selected for use in this first experimental example of the process of the present invention. Specifically, the ACM was a typical "spray-on" fireproofing, and from microscopic analysis included approximately 30% cellulose, 2% glass fiber, traces of talc, fillers and binders. The ACM also included 13% chrysotile asbestos fibers, as determined by the standardized PLM methods, discussed herein and specified in the Asbestos NESHAP. The ACM was placed in a small worm bin 30, having an approximate volume of 1 cubic foot.

6 pounds of worm adjuvant 35 were added to the ACM 22 in the worm bin 30, and mixed by hand. This particular worm adjuvant comprised of a water based mixture steeped with 20% horse manure, 20% paper pulp, 1% molasses 0.25% kelp and 0.5% fish fertilizer, all in approximate quantities by volume, and brewed for at least 12 hours or as needed, and maintained at approximately 70° F. to 90° F., while being gently aerated with a pressurized air stream.

Approximately 3 pounds of *fetida*, "red wiggler" worms 31 were blended into the worm bin 30 and covered with a thin, approximate 1 inch layer of shredded paper. The worms maintained in a substantially dark environment within the closed bin and maintained at a temperature within the bin of approximately 60° F. to 65° F. In a more preferred embodiment of the present invention, higher temperatures than this range are preferable for greater worm activity, as understood by those skilled in vermicomposting. After four months of processing, an additional 3 pounds of *hortensis* worms were supplemented to the worm bin.

The process included the regular maintenance of the vermicompost 32 within the worm bin 30. Every 2 to 3 days, approximately one pound of the worm adjuvant 35 was added to the worm bin over the course of the experiment. Any leachate, herein referred to as process water 51, which drained from the worm bin, was collected and reintroduced back into the worm bin in the recycle stream 52. Each month, the contents of the bin were sampled and analyzed for asbestos fiber counts, again utilizing the PLM method specified in the EPA methods and Asbestos NESHAP. 7 months after the start of the experiment, asbestos fiber levels were below 1%, by PLM, within all samples of the vermicompost.

EXAMPLE 2

5.75 pounds of an ACM 22 was selected for use in this second experimental example of the process of the present invention. Specifically, the ACM was a typical "spray-on" fireproofing, and included approximately 30% cellulose, 2% glass fiber, traces of talc, fillers and binders. The ACM also included 13% chrysotile asbestos fibers, as determined by the standardized PLM methods, discussed herein and specified in the Asbestos NESHAP. The ACM was placed in a small worm bin 30, having an approximate volume of 1 cubic foot.

2 pounds of worm adjuvant 35 were added to the ACM 22 in the worm bin 30, and mixed by hand. As with Example 1, this particular worm adjuvant comprised of a water based mixture steeped with 20% horse manure, 20% paper pulp, 1% molasses 0.25% kelp and 0.5% fish fertilizer, all in approximate quantities by volume, and brewed for at least 12 hours or as needed, and maintained at approximately 70° F. to 90° F., while being gently aerated with a pressurized air stream.

3 pounds of "*fetida*," worms 31 were blended into the worm bin 30 and covered with a thin, approximate 1 inch layer of shredded paper. The worms maintained in a substantially dark environment within the sealed bin and maintained at a temperature within the bin of approximately 60° F. to 65° F. After four months of processing, an additional 3 pounds of *hortensis* worms were supplemented to the worm bin.

The process included the regular maintenance of the vermicompost 32 within the worm bin 30. Every 2 to 3 days, approximately one pound of the worm adjuvant 35 was added to the worm in over the course of the experiment. Any leachate, herein referred to process water 51, that drained from the worm bin was collected and reintroduced back into the worm bin in the recycle stream 52. Each month, the contents of the bin were sampled and analyzed for asbestos fiber counts, again utilizing the PLM method specified in the Asbestos NESHAP. 7 months after the start of the experiment, asbestos fiber levels were below 1%, by PLM, within all samples of the vermicompost.

EXAMPLE 3

Samples of worm castings from the vermicompost 32, formed in the latter stages of experiments 1 and 2, above, were prepared for further examination employing standard PLM techniques. This sample was compared with a sample of unprocessed ACM 22, which was employed as the starting material for the above experiments. The worm castings sample was moist from the worm bin 30, and so was first dried in a glass petri dish and then manually pulverized, then placed on a glass slide, for inspection using the standard PLM techniques. The material was evenly distributed on the slide and set in a high dispersion oil, having a refractive index 1.550. The worm castings contained small amounts of chrysotile asbestos fibers. Specifically, the castings contained 0.25% asbestos fibers, as counted employing "point count" techniques specified for use with PLM per the Asbestos NESHAP. The observed fibers were small in size, with an observed size distribution that centered close to the 5 micron counting threshold. This observation contrasted markedly from the large bundles of long fibers found in the initial ACM sample for the same material prior to processing. These observations showed that the worms were not just encapsulating the asbestos fibers, but actually breaking the fibers down to mineral segments below concern and detection limits.

In examples 1 and 2, above, the product 55 is in itself a safe and potentially asbestos free material, as discussed above. The potential uses for such a product are many, as well understood to those skilled in vermiculture. If the material still contains asbestos, it may be properly disposed of in a landfill.

As an alternative for the generation of a micronized liquid product 89, as shown in FIG. 1, the product from the worm bin 30, or alternatively the worm bin array 30', can be processed with a micronizer 84. The micronizer is preferably a macerator, or alternatively a high shear pump, well known to those skilled in material processing and liquefying. The micronizer receives water, either from a water 43', which is an outside water source, similar to the water 43 discussed above, or alternatively a process water recycle 85 from the process water 51, generated from the worm bin. The micronizer mixes and reduces the size of any materials received, to small micron and sub-micron size ranges.

After the micronizer 84 the macerated and liquified product 55 is preferably filtered by a filter 86. A conventional high efficiency particulate (HEPA) water filter is preferred, as selected for water filtration in asbestos remediation. This step insures that no residual fibers can pass through to the micronized liquid product 89, which, upon certification, can be used or disposed of in a safe manner as non-ACM.

In compliance with the statutes, the invention has been described in language more or less specific as to structural features and process steps. While this invention is susceptible to embodiment in different forms, the specification illustrates preferred embodiments of the invention with the understanding that the present disclosure is to be considered an exemplification of the principles of the invention, and the disclosure is not intended to limit the invention to the particular embodiments described. Specifically,the use of the term "approximately" in the present application is implicitly understood as denoting a certain and specific variation in the stated value that, as understood by a person skilled in the pertinent art, would result in substantially the same result as if the exactly specified value or range were employed. Additionally, those with ordinary skill in the art will appreciate that other embodiments and variations of the invention are possible, which employ the same inventive concepts as described above. Therefore, the invention is not to be limited except by the following claims, as appropriately interpreted in accordance with the doctrine of equivalents.

The following is claimed:

1. A process of asbestos remediational vermiculture comprising the steps of:
   a) placing a regulated asbestos containing material into a bin;
   b) mixing the regulated asbestos containing material with an effective quantity of a worm adjuvant, the worm adjuvant including a supplement for aiding in a vermicultural processing of the regulated asbestos containing material;
   c) introducing a plurality of worms into the regulated asbestos containing material;
   d) forming an asbestos containing vermicompost;
   e) processing the regulated asbestos containing material with the worms, the processing including ingestion of the regulated asbestos containing material by the worms;
   f) forming a vermiprocessed product; and
   g) removing the vermiprocessed product from the bin, the vermiprocessed product having a final average asbestos fiber count, and the asbestos containing vermicompost having an initial average asbestos fiber count, and the final average asbestos fiber count lower than the initial average asbestos fiber count.

2. The process of asbestos remediational vermiculture of claim 1, wherein the step of mixing the regulated asbestos containing material with an effective quantity of a worm adjuvant additionally includes adding a microbial supplement.

3. The process of asbestos remediational vermiculture of claim 1, further including the steps of:
   h) maintaining the static air pressure within the bin at a negative pressure, relative to an ambient static air pressure;
   i) filtering the air stream removed from the bin for asbestos fibers.

4. The process of asbestos remediational vermiculture of claim 1, further including the steps of:
   h) introducing an organic waste into the bin; and
   i) mixing the organic waste with the regulated asbestos containing material.

5. The process of asbestos remediational vermiculture of claim 4, further including the step of:
   j) homogenizing the mixture of the organic waste and the regulated asbestos containing material.

6. The process of asbestos remediational vermiculture of claim 1, further including the step of:
   h) liquefying the vermiprocessed product.

7. The process of asbestos remediational vermiculture of claim 6, further including the step of:
   i) micronizing the vermiprocessed product.

8. The process of asbestos remediational vermiculture of claim 1, wherein the bin is a plurality of bins, including a minimum of a first bin and a second bin, and the step of placing the asbestos containing material into the bin includes:
   a1) placing the asbestos containing material into the first bin for processing; and
   a2) subsequently placing the asbestos containing material into the second bin for processing.

9. A process of asbestos remediational vermiculture comprising the steps of:
   a) placing an asbestos containing material into a bin, the asbestos containing material defined as including asbestos fibers in excess of 1% by weight;
   b) mixing the asbestos containing material with an effective quantity of a worm adjuvant, the worm adjuvant including a supplement for aiding in a vermicultural processing of the asbestos containing material;
   c) introducing a plurality of worms into the asbestos containing material;
   d) forming an asbestos containing vermicompost;
   e) processing the asbestos containing material with the worms, the processing including ingestion of the asbestos containing materials by the worms; and
   f) forming a vermiprocessed product, the vermiprocessed product having no detectable asbestos fibers.

10. The process of asbestos remediational vermiculture of claim 9, wherein the step of mixing the asbestos containing material with an effective quantity of a worm adjuvant additionally includes adding a microbial supplement.

11. The process of asbestos remediational vermiculture of claim 9, further including the steps of:
   g) maintaining the static air pressure within the bin at a negative pressure, relative to an ambient static air pressure;
   h) filtering the air stream removed from the bin for asbestos fibers.

12. The process of asbestos remediational vermiculture of claim 9, further including the steps of:
   g) introducing an organic waste into the bin; and
   h) mixing the organic waste with the asbestos containing material.

13. The process of asbestos remediational vermiculture of claim 12, further including the step of:

i) homogenizing the mixture of the organic waste and the asbestos containing material.

14. The process of asbestos remediational vermiculture of claim 9, further including the step of:

g) liquefying the vermiprocessed product.

15. The process of asbestos remediational vermiculture of claim 14, further including the step of:

h) micronizing the vermiprocessed product.

16. The process of asbestos remediational vermiculture of claim 9, wherein the bin is a plurality of bins, including a minimum of a first bin and a second bin, and the step of placing the asbestos containing material into the bin includes:

a1) placing the asbestos containing material into the first bin for processing; and a2) subsequently placing the asbestos containing material into the second bin for processing.

* * * * *